US006465425B1

(12) United States Patent
Tracy et al.

(10) Patent No.: US 6,465,425 B1
(45) Date of Patent: Oct. 15, 2002

(54) MICROENCAPSULATION AND SUSTAINED RELEASE OF BIOLOGICALLY ACTIVE ACID-STABLE OR FREE SULFHYDRYL-CONTAINING PROTEINS

(75) Inventors: Mark A. Tracy, Arlington, MA (US); Kevin L. Ward, Arlington, MA (US); David S. Scher, Hudson, MA (US); J. Keith Johnson, Hudson, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 0 days.

(21) Appl. No.: 09/501,934

(22) Filed: Feb. 10, 2000

(51) Int. Cl.[7] .............................................. A01N 37/18
(52) U.S. Cl. ................. 514/2; 514/1; 514/724
(58) Field of Search .................. 514/1, 2, 724

(56) References Cited

U.S. PATENT DOCUMENTS

| 4,252,791 A | 2/1981 | Grossberg et al. ............. 424/85 |
| 4,389,330 A | 6/1983 | Tice et al. .............. 427/213.36 |
| 4,462,940 A | 7/1984 | Hanisch et al. .......... 260/112 R |

(List continued on next page.)

FOREIGN PATENT DOCUMENTS

| EP | 0123291 A2 | 4/1984 |
| EP | 0215658 B1 | 9/1986 |
| EP | 0270799 B1 | 10/1987 |

(List continued on next page.)

OTHER PUBLICATIONS

Costantino, H.R., et al., "Solid–Phase Aggregation of Proteins under Pharmaceutically Relevant Conditions," *Journal of Pharmaceutical Sciences*, 83 (12) :1662–1669 (1994).

Constantino, H.R., et al., "Aggregation of a Lyophilized Pharmaceutical Protein, Recombinant Human Albumin. Effect of Moisture and Stabilization by Excipients," *Biotechnology*, 13:493–496 (1995).

Liu, W.R., et al., "Moisture–Induced Aggregation of Lyophilized Proteins in the Solid State," *Biotechnology and Bioengineering*, 37:177–184 (1991).

Lu, W., et al., "Protein Release from Poly(lactic–co–glycolic acid) Microspheres: Protein Stability Problems," *PDA Journal of Pharmaceutical Science & Technology*, 49 (1):13–19 (1995).

Cleland, J.L., et al., "In Vitro Release of Bioactive Recombinant Human Interferon–γ From PLGA Microspheres," *Proceed. Intern. Symp. Control. Rel. Bioac. Mater.*, 22:518–519 (1995).

Phillips, L., "Beta–Interferon: An Exciting New Agent for Multiple Sclerosis," CPJ/RPC, 237, 240, 242 and 252 (Jun. 1994).

(List continued on next page.)

*Primary Examiner*—Jezia Riley
(74) *Attorney, Agent, or Firm*—Hamilton, Brook, Smith and Reynolds, P.C.

(57) ABSTRACT

This invention relates to sustained release compositions, and methods of forming and using said compositions, for the sustained release of biologically active acid-stable or free sulfhydryl-containing proteins, in particular β-IFN. The sustained release composition of this invention comprises a biocompatible polymer having dispersed therein a stabilized biologically active acid-stable or free sulfhydryl-containing protein formulation and a nonionic polymer surfactant.

53 Claims, 3 Drawing Sheets

U.S. PATENT DOCUMENTS

| | | | |
|---|---|---|---|
| 4,711,782 A | 12/1987 | Okada et al. | 424/455 |
| 4,767,628 A | 8/1988 | Hutchinson | 424/426 |
| 4,818,542 A | 4/1989 | DeLuca et al. | 424/491 |
| 4,853,218 A | 8/1989 | Yim et al. | 424/85.7 |
| 4,871,538 A | 10/1989 | Yim et al. | 424/85.7 |
| 4,962,091 A | 10/1990 | Eppstein et al. | 514/2 |
| 4,992,271 A | 2/1991 | Fernandes et al. | 424/85.2 |
| 5,004,605 A | 4/1991 | Hershenson et al. | 424/85.6 |
| 5,019,400 A | 5/1991 | Gombotz et al. | 424/497 |
| 5,126,147 A | 6/1992 | Silvestri et al. | 424/497 |
| 5,176,907 A | 1/1993 | Leong | 424/78.08 |
| 5,316,774 A | 5/1994 | Eury et al. | 424/501 |
| 5,441,734 A | 8/1995 | Reichert et al. | 424/85.7 |
| 5,594,091 A | 1/1997 | Igari et al. | 528/271 |
| 5,643,566 A | 7/1997 | Hanisch et al. | 424/85.4 |
| 5,656,297 A | 8/1997 | Bernstein et al. | 424/484 |
| 5,711,968 A | 1/1998 | Tracy et al. | 424/487 |
| 5,874,479 A * | 2/1999 | Martin | 514/724 |
| 5,922,253 A | 7/1999 | Herbert et al. | 264/5 |

FOREIGN PATENT DOCUMENTS

| | | |
|---|---|---|
| EP | 0 251 476 | 1/1988 |
| EP | 0281299 A1 | 2/1988 |
| EP | 0307097 A2 | 8/1988 |
| EP | 0330180 A1 | 2/1989 |
| FR | 2 620 621 | 3/1989 |
| WO | WO 90/09166 | 8/1990 |
| WO | WO 90/13285 | 11/1990 |
| WO | WO 90/13780 | 11/1990 |
| WO | WO 91/12882 | 9/1991 |
| WO | WO 91/18927 | 12/1991 |
| WO | WO 94/19373 | 9/1994 |
| WO | WO 96/03116 | 2/1996 |
| WO | WO 96/28143 | 9/1996 |
| WO | WO 96/40074 | 12/1996 |
| WO | WO 97/13502 | 4/1997 |
| WO | WO 98/27963 | 7/1998 |
| WO | WO 99/24061 | 5/1999 |

OTHER PUBLICATIONS

Gekko, K., et al., "Compressibility–Structure Relationship of Globular Proteins," *Biochemistry*, 25:6563–6571 (1986).

Hanley, D.F., et al., "Pharmacology of Interferons I. Pharmacologic Distinctions Between Human Leukocyte and Fibroblast Interferons," *J. Immunopharmac.*, 1:219–226 (1979).

Hosoi, K., et al., "Structural Characterization of Fibroblast Human Interferon–$\beta_1$," *Journal of Interferon Research*, 8 : 375–384 (1998).

Rubinstein, M., "The Structure of Human Interferons," *Biochimica et Biophysica. Acta.*, 695:5–16 (1982).

Yu–Chang, J.W., and Hanson, M.A., "Parenteral Formulations of Proteins and Peptides: Stability and Stabilizers," *Journal of Parenteral Science and Technology*, 42 (2S):S4–S27 (1988).

Billiau, A., et al., "Human Fibroblast Interferon for Clinical Trials: Pharmacokinetics and Tolerability in Experimental Animals and Humans," *Antimicrobial Agents and Chemotherapy*, 16(1):56–63 (1979).

* cited by examiner

MICROENCAPSULATION AND SUSTAINED RELEASE OF BIOLOGICALLY ACTIVE ACID-STABLE OR FREE SULFHYDRYL-CONTAINING PROTEINS

BACKGROUND OF THE INVENTION

Numerous acid-stable or free sulfhydryl-containing proteins, such as βIFN, exhibit biological activity in vivo, which renders them useful as medicaments in therapy. Many illnesses or conditions which can be treated with this type of protein, for example, Multiple Sclerosis (MS) which is currently treated with β-IFN, require administration of a constant or sustained level of medicament to provide the most effective prophylactic and/or therapeutic effects. For example, BETASERON® (Interferon beta-1b) is currently administered for the treatment of MS at a dose of 9 million IU, injected subcutaneously three time a week. As such, administration of biologically active acid-stable or free sulfhydryl-containing proteins requires frequent subcutaneous injections, which result in fluctuating levels of medicament and poor patient compliance.

As an alternative, the use of biodegradable materials, such as polymers, encapsulating the medicament can be employed as a sustained delivery system. The use of biodegradable polymers, for example, in the form of microparticles or microcarriers, can provide a sustained release of medicament, by utilizing the inherent biodegradability of the polymer to control the release of the medicament thereby providing a more consistent, sustained level of medicament and improved patient compliance.

However, these sustained release devices can exhibit high initial bursts of medicament and minimal release thereafter. In addition, due to the high solution concentration of medicament within and localized around these sustained release devices, the medicament can aggregate thereby increasing immunogenicity in vivo and interfering with the desired release profile for the medicament. Further, methods used to form sustained release compositions can result in loss of activity of the medicament due to the instability of the medicament and the degradative effects of the processing steps. In addition, adsorption of the biologically active acid-stable or free sulfhydryl-containing proteins onto the polymer surface can inhibit the release from the sustained release composition.

Therefore, a need exists for a means of administering biologically active acid-stable or free sulfhydryl-containing proteins, for example, β-IFN in a sustained fashion wherein activity and potency of the protein is maintained.

SUMMARY OF THE INVENTION

This invention relates to compositions for the sustained release of biologically active acid-stable or free sulfhydryl-containing proteins, and methods of forming and using said compositions, for the sustained release of biologically active acid-stable or free sulfhydryl-containing proteins, in particular, β-IFN. The sustained release compositions of this invention comprise a biocompatible polymer having dispersed therein a stabilized biologically active acid-stable or free sulfhydryl-containing protein formulation, and at least one surfactant. The stabilized biologically active acid-stable or free sulfhydryl-containing protein formulation of the sustained release composition comprises at least one biologically active acid-stable or free sulfhydryl-containing protein, at least one disaccharide and at least one acidic excipient Optionally, the stabilized biologically active acid-stable or free sulfhydryl-containing protein formulation further comprises a water soluble polymer.

The method of the invention, for forming a composition for the sustained release of biologically active acid-stable or free sulfhydryl-containing proteins, includes dissolving a biocompatible polymer in a polymer solvent to form a polymer solution, adding at least one surfactant and the stabilized biologically active acid-stable or free sulfhydryl-containing protein formulation to the polymer solution, and then solidifying the polymer to form a polymer matrix containing the stabilized biologically active acid-stable or free sulfhydryl-containing protein formulation and the surfactant dispersed therein.

The method of using the sustained release composition of the present invention comprises providing a therapeutically effective blood level of biologically active acid-stable or free sulfhydryl-containing protein, in particular, β-IFN in a subject for a sustained period by administering to the subject a dose of the sustained release composition described herein.

The sustained release composition of the invention overcomes the problem of aggregation of the biologically active acid-stable or free sulfhydryl-containing protein, for example, β-IFN which can occur during processing and/or following administration in vivo, when the biologically active protein is not stabilized. Further, loss of activity of the biologically active protein due to instability of the medicament, and chemical interactions between the biologically active protein and other components, which are contained in or used in formulating the sustained release composition, are minimized.

The advantages of the sustained release formulation for biologically active acid-stable or free sulfhydryl-containing proteins, in particular, β-IFN as described herein, include increased patient compliance and acceptance by eliminating the need for repetitive administration, increased therapeutic benefit by eliminating fluctuations in active agent concentration in blood levels by providing a desirable release profile, and a potential lowering of the total amount of biologically active acid-stable or free sulfhydryl-containing protein necessary to provide a therapeutic benefit, by reducing these fluctuations.

DETAILED DESCRIPTION OF THE INVENTION

The sustained release compositions of this invention comprise a biocompatible polymer having dispersed therein a stabilized biologically active acid-stable or free sulfhydryl-containing protein formulation, and at least one surfactant. The stabilized biologically active acid-stable or free sulfhydryl-containing protein formulation of the sustained release composition comprises at least one biologically active acid-stable or free sulfhydryl-containing protein, at least one disaccharide and at least one acidic excipient. Optionally, the stabilized biologically active protein formulation further comprises a water soluble polymer.

The method of the invention, for forming a composition for the sustained release of biologically active acid-stable or free sulfhydryl-containing proteins, includes dissolving a biocompatible polymer in a polymer solvent to form a polymer solution, adding a surfactant and the stabilized biologically active acid-stable or free sulfhdryl-containing protein formulation, to the polymer solution, and then solidifying the polymer to form a polymer matrix containing the stabilized biologically active acid-stable or free sulfhydryl-containing protein formulation and surfactant dispersed therein.

The method of using the sustained release composition of the present invention comprises providing a therapeutically effective blood level of biologically active acid-stable or free sulfhydryl-containing protein, in particular, β-IFN in a subject for a sustained period by administering to the subject a dose of the sustained release composition described herein.

"Biologically active acid-stable or free sulfhydryl-containing protein" as that term is used herein are proteins which are stable under acidic conditions or contain a free sulfhydryl group. Acid-stable or free sulfhydryl-containing proteins suitable for use in the invention include, but are not limited to, IL-2, basic fibroblast growth factor, granulocyte colony stimulating factor, β-IFN and muteins of β-IFN, for example, IFN-$β_{ser17}$, MGDF (megakaryocyte growth and differentiation factor), TPA (tissue plasminogen activator), IGF-1 (insulin-like growth factor-1) and IL-1β (interleukin -1β).

Proteins containing a free sulfhydryl can be determined using, reagents which detect the presence of the free sulfhydryl. Such a reagent is Ellman's reagent (5,5'-dithiobis (2-nitrobenzoic acid)) also referred to as DTNB. DTNB reacts with free sulfhydryls to give mixed disulfides plus 2-nitro-5-thiobenzoic acid (TNB) which can be quantified by its absorbance at 412 nm.

Acid stable proteins can be determined by incubating the protein under acidic conditions for a predetermined period of time and then evaluating the integrity of the protein by, for example, electrophoresis and/or circular dichroism. Proteins which do not exhibit significant degradation can be defined as acid stable. Degradation includes, for example, dimerization, particularly oxidative dimerization, and/or aggregation of the protein which can lead to an undesirable decrease in solubility. Preferably dimer formation is less than about 10%.

"β-IFN" or "β-interferon" as that term is used herein is an acid-stable or free sulfhydryl-containing protein which is synthesized by mammalian cells in response to viral infection, immune stimulation and other factors. β-IFN has a molecular weight of between 18,000 and 23,000 daltons depending on the particular form, and is characterized by three cysteine amino acids, two of which are linked in a disulfide bond leaving one remaining as a free sulfhydryl (cysteine 17). β-IFN includes β-IFN derived both from natural sources, including human, bovine, canine, feline, porcine and equine, and by recombinant DNA techniques. The term also includes modified forms of β-interferon, for example, wherein glycosylation, methylation, substitution and/or deletion of a specified number of amino acids has occurred. IFN-$β_{ser17}$ refers to β-IFN in which the seventeenth amino acid present in the sequence (cysteine) has been replaced by senne.

As defined herein, a sustained release of biologically active acid-stable or free sulfhydryl-containing protein is a release of the protein from the sustained release composition of the invention which occurs over a period which is longer than that period during which a biologically significant amount of the protein, for example, β-IFN would be available following direct administration of a solution of the protein. It is preferred that a sustained release be a release of acid-stable or free sulfhydryl-containing protein which occurs over a period of greater than two days. A sustained release of acid-stable or free sulfhydryl-containing protein from a polymeric matrix can be a continuous or a discontinuous release, with relatively constant or varying rates of release. The continuity of release and level of release can be affected by the type of polymer composition used (e.g., monomer ratios, molecular weight, block composition, and varying combinations of polymers), protein loading, and/or selection of excipients to produce the desired effect.

A "therapeutically or prophylactically effective amount", as used herein, is the amount of the composition for the sustained release of a biologically active acid-stable or free sulfhydryl-containing protein, for example, β-IFN, necessary to elicit the desired biological response following administration.

"Stabilized biologically active acid-stable or free sulfhydryl-containing protein formulation", as that term is used herein, refers to a biologically active acid-stable or free sulfhydryl-containing protein, for example, β-IFN which can be stabilized against degradation, aggregation, loss of potency and/or loss of biological activity, all of which can occur during formation of the sustained release composition, and prior to and/or during in vivo release. For example, β-IFN and other acid-stable or free sulfhydryl-containing proteins can aggregate to form a dimer which is not biologically active. The dimer can be formed during processing of the sustained release composition or following administration in vivo. When the protein contains a free sulfhydryl, formation of covalent aggregates can result from intermolecular disulfide formation.

In addition, interactions between the biologically active acid-stable or free sulfhydryl-containing protein and the biocompatible polymer of the sustained release composition can shorten the period of sustained release. For example, it has been determined that β-IFN adsorbs onto the polymer of the sustained release composition resulting in an undesirable release profile. Furthermore, proteins which are acid-stable can be significantly degraded when exposed in vivo to physiological pH (7.4) for sustained periods of time.

Stabilization of the biologically active acid-stable or free sulfhydryl-containing protein, for example, β-IFN can be accomplished, for example, by the use of a particular combination of stabilizing agents. "A stabilizing agent" as that term is used herein, is any agent which binds or interacts in a covalent or non-covalent manner, or is included with the protein, for example, β-IFN to stabilize against degradation, loss of post hydration solubility, loss of potency and/or loss of biological activity. Stabilizing agents can also be added to the sustained release composition which minimize the undesired interaction of the protein with the biocompatible polymer, for example, adsorption of the acid-stable or free sulfhydryl-containing protein to the surface of the biocompatible polymer of the sustained release composition.

A "stabilized biologically active acid-stable or free sulfhydryl-containing protein formulation," as defined herein, comprises at least one acid-stable or free sulfhydryl-containing protein in combination with at least one disaccharide, and at least one acidic excipient. Optionally, at least one water soluble polymer can also be present in the stabilized protein formulation. The sustained release composition comprises the stabilized biologically active acid-stable or free sulfhydryl-containing protein formulation, a biocompatible polymer and at least one surfactant which is dispersed in the polymer phase. The water soluble polymer, optionally present in the stabilized biologically active protein formulation, can in some instances be the same as the surfactant present in the polymer phase. The amount of biologically active acid-stable or free sulfhydryl-containing protein in the stabilized biologically active protein formulation can range from about 0.5% (w/w) to about 50% (w/w) of the dry stabilized biologically active protein formulation. For example, from about 0.5% (w/w) to about 30% (w/w), or more specifically from about 2% (w/w) to about 20% (w/w).

"Acidic excipient" as that term is used herein refers to any organic acid. These excipients can be added as the acid, or as the salt form of the conjugate base of the acid. For example, the acidic excipient citric acid can be added either in the acid form, citric acid, or as the salt form of the conjugate base, for example, the mono-, di-, or trisodium salt of the citric acid. Suitable acidic excipients include citric acid, ascorbic acid, acetic acid, ethylenediaminetetraacetic acid, saturated fatty acids, bile acids, dicarboxylic acids, and combinations thereof. Suitable saturated fatty acids include, but are not limited to butyric, caproic, caprylic, capric, lauric, myristic, palmitic, stearic and arachadic. Suitable bile acids include cholic acid, taurocholic acid, deoxycholic acid, taurodeoxycholic acid, chenodeoxycholic acid, glycocholic acid, glycodeoxycholic, and lithocholic acid. Suitable dicarboxylic acids include, but are not limited to oxalic, malonic, succinic, glutaric, adipic, pimelic, suberic, azelaic, and sebacic. Particular acidic excipients suitable for use in the invention include amino acids. Preferred amino acids are the acidic amino acids. "Acidic amino acids" as that term is used herein, refers to amino acids having acidic side chains, thereby resulting in the presence of more acidic groups than basic groups. For example, aspartic acid and glutamic acid are acidic amino acids. These particular amino acids are typically referred to as aspartate and glutamate to emphasize that their side chains are nearly always negatively charged at physiological pH. The amount of acidic excipient present in the stabilized biologically active acid-stable or free sulfhydryl-containing protein formulation can range from about 1% (w/w) to about 50% (w/w) of the dry stabilized biologically active protein formulation, for example from about 2% (w/w) to about 20% (w/w).

A "disaccharide", as defined herein, is a compound which upon hydrolysis yields two molecules of a monosaccharide. Suitable disaccharides include, but are not limited to, sucrose and trehalose. It is preferred that the disaccharide is non-reducing. The mount of disaccharide present in the stabilized biologically active acid-stable or free sulfhydryl-containing protein formulation can range from about 5% to about 95%.

"Surfactants" as that term is used herein refers to any substance which can reduce the surface tension between immiscible liquids. Suitable surfactants include, polymer surfactants, such as nonionic polymer surfactants, for example, poloxamers, polysorbates, polyethylene glycols (PEGs), polyoxyethylene fatty acid esters, polyvinylpyrrolidone and combinations thereof. Examples of poloxamers suitable for use in the invention include poloxamer 407 sold under the trademark PLURONIC® F127 and poloxamer 188 sold under the trademark PLURONIC® F68, both available from BASF Wyandotte. Examples of polysorbates suitable for use in the invention include polysorbate 20 sold under the trademark TWEEN® 20 and polysorbate 80 sold under the trademark TWEEN® 80. Cationic surfactants, for example, benzalkonium chloride, are also suitable for use in the invention. In addition, bile salts, such as deoxycholate and glycocholate are suitable as surfactants based on their highly effective nature as detergents.

As described in the Experimental Section, the surfactant assists in minimizing adsorption of the acid-stable or free sulfhydryl-containing protein to the biocompatible polymer of the polymer matrix. It has been found that in addition to the surfactant, the presence of an acidic excipient in the polymer phase of the sustained release composition described herein can increase the anti-adsorption effect seen with the surfactant. The amount of surfactant present in the polymer of the sustained release composition can range from about 1% w/w to about 40% w/w of the total weight of the composition.

A "water soluble polymer" as defined herein is any polymer which is soluble in water. In a preferred embodiment, the water soluble polymer is also soluble in the polymer solvent used in the process for preparing the sustained release composition described herein. Water soluble polymers suitable for use in the invention include water soluble polysaccharides, for example, methyl cellulose, ethyl cellulose, ficoll and combinations thereof, and nonionic polymer surfactants such as poloxamers, for example poloxamer 407, poloxamer 188 and combinations thereof, and polysorbates, for example, polysorbate 80, polysorbate 20, polyethylene glycol polymers, polyvinylpyrrolidone, polyoxyethylene fatty acid esters and any combination thereof.

When present in the stabilized biologically active acid-stable or free sulfhydryl-containing protein formulation the water soluble polymer can range from about 0.5% (w/w) to about 40% (w/w) of the dry weight of the stabilized formulation.

In a specific embodiment, the stabilized biologically active acid-stable or free sulfhydryl-containing protein formulation is stabilized β-IFN comprising β-IFN, glutamate and trehalose. The β-IFN can be present in the stabilized biologically active β-IFN in a range of from about 1% w/w to about 30% w/w of the dry weight of the stabilized β-IFN formulation. The glutamate can be present in the stabilized biologically active β-IFN in a range of from about 1% w/w to about 30% w/w of the dry weight of the stabilized β-IFN formulation. The trehalose can be present in the stabilized biologically active β-IFN in a range of from about 20% w/w to about 90% w/w of the dry weight of the stabilized β-IFN formulation. When the optional water soluble polymer is present it can be present in an amount from about 0.5% w/w to about 40% w/w of the dry weight of the stabilized β-IFN formulation.

Polymers suitable to form the sustained release composition of this invention are biocompatible polymers which can be either biodegradable or non-biodegradable polymers or blends or copolymers thereof. A polymer is biocompatible if the polymer and any degradation products of the polymer are non-toxic to the recipient and also possess no significant deleterious or untoward effects on the recipient's body, such as an immunological reaction at the injection site.

"Biodegradable", as defined herein, means the composition will degrade or erode in vivo to form smaller chemical species. Degradation can result, for example, by enzymatic, chemical and physical processes. Suitable biocompatible, biodegradable polymers include, for example, poly (lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl flouride, poly(vinyl imidazole), chlorosulphonate polyolefins, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons. In a preferred embodiment, the polymer is biodegradable polymer or copolymer. In a more preferred embodiment, the polymer is a poly(lactide-co-glycolide)(hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 5,000 Daltons to about 42,000 Daltons.

To prepare stabilized biologically active acid-stable or free sulfhydryl-containing protein formulations, such as a stabilized biologically active β-IFN formulation, at least one protein is mixed in an aqueous solution comprising at least one disaccharide and at least one acidic excipient. Optionally, at least one water soluble polymer can be included. The resulting solution is then spray freeze dried to form the stabilized biologically active acid-stable or free sulfhydryl-containing protein formulation, for example, β-IFN. Spray freeze drying of the solution can be accomplished by atomizing the solution to form liquid droplets, contacting the liquid droplets with a freezing medium to produce frozen droplets, removing the solvent from the frozen droplets to form a stabilized biologically active acid-stable or free sulfhydryl-containing protein formulation. The solvent can be removed from the droplets by, for example, lyophilization.

Preferably, the formulation comprises particles of stabilized biologically active cid-stable or free sulfhydryl-containing protein, for example, β-IFN, having a volume edian particle size of 10 micrometers or less. The stabilized β-IFN and other stabilized protein particles can be fragmented separately, as described in co-pending U.S. patent application Ser. No. 08/006,682, filed Jan. 21, 1993, which describes a process for producing small particles of biologically active agents, the entire content of which is incorporated herein by reference. Alternatively, the stabilized β-IFN or other stabilized protein particles can be fragmented after being added to a polymer solution as part of the process for producing the sustained release composition described herein. Fragmentation can be accomplished, for example, by means of an ultrasonic probe, homogenization, mechanical shear, or ultrasonic nozzle.

It has been found that addition of a water soluble polymer to the solution which is spray freeze dried to form the biologically active acid stable or free sulfhydryl-containing protein formulation can result in a reduction in the volume median particle size of the stabilized biologically active acid-stable or free sulfhydryl-containing protein formulation. More specifically, subsequent fragmentation of the stabilized biologically active acid-stable or free sulfhydryl-containing protein formulation, in a solvent which is a nonsolvent for the protein but a solvent for the water soluble surfactant and biocompatible polymer of the resulting sustained release composition, can achieve this reduction in particle size. In a preferred embodiment, the water soluble polymer is a nonionic water soluble polymer surfactant which is likewise soluble in the solvent for the biocompatible polymer of the sustained release composition. Use of a water soluble polymer as a means of reducing the particle size of biologically active agent is described in detail in U.S. application Serial No. 09/501,636 entitled "A Method of Preparing a Sustained Release Composition and Use Thereof" filed on Feb. 10, 2000 and incorporated herein by reference.

The amount of biologically active acid-stable or free sulfhydryl-containing protein, for example β-IFN, which is contained within the polymeric matrix of a controlled release composition, is a therapeutically or prophylactically effective amount which can be determined by a person of ordinary skill in the art, taking into consideration factors such as body weight, condition to be treated, type of polymer used, and release rate from the polymer.

Typically, the sustained release composition can contain from about 0.01% (w/w) to about 30% (w/w) of the biologically active acid-stable or free sulfhydryl-containing protein (dry weight of composition). The amount of the acid-stable or free sulfhydryl-containing protein will vary depending upon the desired effect of the acid-stable or free sulfhydryl-containing protein, the planned release levels, and the time span over which the protein, for example β-IFN will be released. A specific range of loading is between about 0.1% (w/w) to about 10% (w/w) such as 0.5% (w/w) to about 5% (w/w).

It is understood that the amount of stabilized biologically active acid-stable or free sulfhydryl-containing protein formulation needed to achieve a theoretical load of protein in the sustained release composition can be determined based on the percentage of protein present in the formulation. For example, if a theoretical protein load of 1% is desired in the sustained release composition and the stabilized biologically active acid-stable or free sulfhydryl-containing protein formulation contains 10% protein, then the final sustained release composition should contain 10% (w/w) of the formulation.

Bulking agents can also be present in the sustained release composition of the invention. Typically these bulking agents comprise inert materials. Suitable bulking agents are known to those skilled in the art.

A metal cation component which is dispersed within the polymer matrix can also be used as an optional excipient. This metal cation component acts to further modulate the release of the acid-stable or free sulfhydryl-containing protein and is not complexed with the protein. A metal cation component used in modulating release typically comprises at least one type of multivalent metal cation. Examples of metal cation components suitable to modulate protein release include or contain, for example, $Mg(OH)_2$, $MgCO_3$ (such as $4MgCO_3Mg(OH)_25H_2O$), $MgSO_4$, $Zn(OAc)_2$, ZnSO$_4$, ZNCl$_2$, MgCl$_2$ and magnesium citrate. A suitable ratio of metal cation component to polymer is between about 1:99 to about 1:2 by weight. The optimum ratio depends upon the polymer and the metal cation component utilized. A polymeric matrix containing a dispersed metal cation component to modulate the release of a biologically active agent from the polymeric matrix is further described in U.S. Pat. No. 5,656,297 and co-pending U.S. patent application Ser. No. 08/1727,531, the teachings of both of which are incorporated herein by reference in their entirety.

The sustained release composition of this invention can be formed into many shapes such as a film, a pellet, a cylinder, a disc or a microparticle. A microparticle, as defined herein, comprises a polymer component having a diameter of less than about one millimeter and having stabilized biologically active acid-stable or free sulfhydryl-containing protein, for example, β-IFN dispersed or dissolved therein. A microparticle can have a spherical, non-spherical or irregular shape. Typically, the microparticle will be of a size suitable for injection. A typical size range for microparticles is 1000 microns or less. In a particular embodiment, the microparticle ranges from about one to about 180 microns in diameter.

In the method of this invention for forming a composition for the sustained release of a biologically active acid-stable or free sulfhydryl-containing protein, for example, β-IFN, a predetermined amount of particles of stabilized biologically active acid-stable or free sulfhydryl-containing protein formulation is dispersed in a polymer solution. The amount of formulation is determined based on the load of protein desired.

A suitable polymer solution contains between about 1% (w/v) and about 30% (w/v) of a suitable biocompatible polymer, wherein the biocompatible polymer is typically dissolved in a suitable polymer solvent. Preferably, a polymer solution contains about 2% (w/v) to about 20% (w/v) polymer.

A suitable polymer solvent, as defined herein, is a solvent in which the polymer is soluble, in which some, none, or all of the stabilized biologically active acid-stable or free sulfhydryl-containing protein formulation is soluble and in which the formulation is non-reactive. Examples of suitable polymer solvents include polar organic liquids, such as methylene chloride, chloroform, ethyl acetate, methyl acetate, hexafluoroisopropanol, acetone, dimethylsulfoxide and combinations thereof.

One suitable method for forming sustained release microparticles from a polymer solution is described in U.S. Pat. No. 5,019,400, issued to Gombotz et al., and U.S. Pat. No. 5,912,253 issued to Herbert et al., the teachings of which are incorporated herein by reference in their entirety. This method of microparticle formation, as compared with other methods such as phase separation, can also reduce the amount of biologically active acid-stable or free sulfhydryl-containing protein, such as β-IFN, required to produce a sustained release composition with a specific biologically active protein content.

In this method, a polymer solution, containing the stabilized biologically active β-IFN or other stabilized biologically active acid-stable or free sulfhydryl-containing protein formulation which can be present in solution or as a particle dispersion, is processed to create droplets, wherein at least a significant portion of the droplets contains polymer, polymer solvent and the stabilized β-IFN or other biologically active acid-stable or free sulfhydryl-containing protein particles. These droplets are then frozen by means suitable to form microparticles. Examples of means for processing the mixture comprising a polymer solution and the stabilized biologically active β-IFN formulation or other biologically active acid-stable or free sulfhydryl-containing protein formulation to form droplets include directing the dispersion through an ultrasonic nozzle, pressure nozzle, Rayleigh jet, or by other known means for creating droplets from a solution.

Means suitable for freezing droplets to form microparticles include directing the droplets into or near a liquified gas, such as liquid argon or liquid nitrogen to form frozen microdroplets which are then separated from the liquid gas. It is to be understood that the stabilized biologically active β-IFN formulation can be spray freeze dried following the above described procedure.

The frozen microdroplets are then exposed to a liquid or solid non-solvent, such as ethanol, hexane, ethanol mixed with hexane, heptane, ethanol mixed with heptane, pentane or oil. The solvent in the frozen microdroplets is extracted as a solid and/or liquid into the non-solvent to form stabilized β-IFN or other stabilized biologically active acid-stable or free sulfhydryl-containing protein containing microparticles. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release microparticles can be made by varying the droplet size, for example, by changing the ultrasonic nozzle frequency. If very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter. The particles can be isolated from the extraction solvent by filtration and can be dried by evaporation to further remove remaining solvent. The particles can be sized by passing them through an appropriately sized mesh.

Yet another method of forming sustained release composition, from a polymer solution, includes film casting, such as in a mold, to form a film or a shape. For instance, after putting the polymer solution containing a stabilized biologically active acid-stable or free sulfhydryl-containing protein formulation into a mold, the polymer solvent is then removed by means known in the art, or the temperature of the polymer solution is reduced, until a film or shape, with a consistent dry weight, is obtained. Film casting of a polymer solution, containing a biologically active agent, is further described in U.S. Pat. No. 5,656,297, the teachings of which are incorporated herein by reference in their entirety.

Without being bound by a particular theory it is believed that the release of the iologically active acid-stable or free sulfhydryl-containing protein, for example, β-IFN, an occur by two different mechanisms. First, the biologically active acid-stable or free sulfhydryl-containing protein can be released by diffusion through aqueous filled channels generated in the polymeric matrix, such as by the dissolution of the protein, or by voids created by the removal of the polymer solvent during the preparation of the sustained release composition. A second mechanism is the release of the protein, for example β-IFN, due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. By altering the properties of the polymer, the contributions of diffusion and/or polymer degradation to release can be controlled. For example, increasing the glycolide content of a poly(lactide-co-glycolide) polymer and/or decreasing the molecular weight of the polymer can enhance the hydrolysis of the polymer and thus, provides an increased rate of release of protein due to polymer erosion.

In addition, the rate of polymer hydrolysis is increased in non-neutral pH. Therefore, an acidic or a basic excipient can be added to the polymer solution, used to form the microparticle, to alter the polymer erosion rate.

The composition of this invention can be administered to a human, or other animal, by injection, implantation (e.g., subcutaneously, intramuscularly, intraperitoneally, intracranially, and intradermally), administration to mucosal membranes (e.g., intranasally, intravaginally, intrapulmonary or by means of a suppository), or in situ delivery (e.g., by enema or aerosol spray) to provide the desired dosage of biologically active acid-stable or free sulfhydryl-containing protein, for example β-IFN, based on the known parameters for treatment with such protein of the various medical conditions.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and scope of the invention be embraced by the defined claims.

The invention will now be further and specifically described by the following examples.

Exemplifications

The following methods were employed to analyze samples produced during the production and characterization of the β-IFN containing microparticles. For example, the bulk drug can be analyzed, β-IFN lyophilizates can be analyzed, β-IFN extracted from the microparticles can be analyzed, as well as protein released from the microparticles.

Methods of Analysis

Size Exclusion Chromatography

Size Exclusion Chromatography (SEC) was employed to determine the % of native monomeric β-IFN in an aqueous solution. SEC was conducted on a 7.8 mm×30 cm TSK G2000SWXL 5 μm column available from Supelco (Cat. #: 08540) using a precolumn filter. The flow rate was 0.5 mL/min with a column load of between 0.1 and 30 μg and a detector setting of 214 nm. The elution system was isocratic using 30% MeCN/0.2% TFA.

Reversed Phase HPLC (RPHPLC)

Reversed Phase HPLC was used to determine the purity of β-IFN samples isolated at various stages as detailed above. Specifically, the quantity of oxidized beta-IFN was determined employing this method. RPHPLC was conducted on a 4.6 mm×250 mm Supelco C4 5 μm Supelcosil LC-304 column available from Supelco (Part #: 5-8824). The flow rate was 1 mL/min with a run time of 70 minutes. A column load of between 0.5 μg and 30 μg and a detector setting at 214 nm. The elution system consisted of Mobile Phase A (40% MeCN/0.14% HFBA(n-heptafluorobutyric acid), Mobile Phase B (80% MeCN/0.14% HFBA) and Mobile Phase C (80% MeCN/0.1% TFA) employing the following gradient:

| 0'  | 70%A | 30%B  |       |
|-----|------|-------|-------|
| 5'  | 70%A | 30%B  |       |
| 58' | 62%A | 38%B  |       |
| 63' | 0%A  | 100%B |       |
| 68' | 0%A  | 0%B   | 100%C |
| 69' | 70%A | 30%B  |       |

SDS-Page

As a complement to the SEC method described above, an SDS-PAGE method performed under non-reducing conditions was employed to measure covalent aggregation of β-IFN in lyophilizate samples compared to the bulk drug. Samples were reconstituted in 50 mM sodium acetate buffer (pH 3.8) at a concentration of about 0.4 mg/mL. The solution or suspension was sampled and then diluted to 0.3 mg/mL with a 4×Novex SDS solubilization solution, available from Novex, Inc. After boiling for 5 minutes, solutions were allowed to cool to room temperature and 4 uL was applied to an 8–15% Gradient Phast Gel with SDS-buffer blocks. The separation and Coomassie staining were performed by the Standard Phast System protocol available from Amersham Pharmacia. Gels were scanned using a laser densitometer and relative amounts monomer, dimer, and aggregate were quantitated. The results were compared to the bulk drug carried through the same SDS-PAGE sample preparation procedure.

ELISA

The amount of β-IFN in rat serum was determined using an ELISA kit available from Toray-Fuji Bionics, Inc. (TFB, Inc.). The kit utilizes the one step sandwich method for the quantitation of β-IFN in serum.

Extraction of β-IFN from Microparticles

The following procedure was employed to extract β-IFN from poly(lactide-co-glycolide) microparticles in order to determine the integrity of the drug post-encapsulation. The procedure was performed at room temperature and used an extraction buffer composed of 80% acetic acid and 0.5% TWEEN 80. One and a half milliliters of this extraction buffer was added to a 10 mg sample of the microspheres and it was vortexed for about 5 minutes. The acetic acid dissolved both the polymer and the protein. The sample was centrifuged to remove any remaining particles. 300 μL of the resulting supernatant was transferred to a tube containing 1200 μL of water to precipitate the polymer. The tube was vortexed for about 10 seconds and centrifuged for about 10 minutes to remove the precipitated polymer. The supernatant was analyzed by SEC to determine protein integrity.

Preparative Methods

Polymer

The polymers employed in the following examples were purchased from Alkermes, Inc. of Cincinnati, Ohio and can be described as follows:

Polymer A: Cat. No.: 5050 2M; Poly(lactide-co-glycolide; 50:50 lactide:glycolide ratio; 10 kD Mol. Wt.; Esterified end group.

Polymer B: Cat. No.: 5050 2A; Poly(lactide-co-glycolide; 50:50 lactide:glycolide ratio; 10 kD Mol. Wt.; Carboxylic acid end group.

Polymer C: Cat. No.: 5050 4A; Poly(lactide-co-glycolide; 50:50 lactide:glycolide ratio; 40 kD Mol. Wt.; Carboxylic acid end group.

Polymer D: Cat. No.: 8515 2A; Poly(lactide-co-glycolide; 85:15 lactide:glycolide ratio; 10 kD Mol. Wt.; Carboxylic acid end group.

Process for Preparing Microparticles

Formation of a polymer solution by dissolving polymer in a suitable polymer solvent.

Addition of a nonionic surfactant to the polymer phase.

Addition of the stabilized biologically active acid-stable or free sulfhydryl-containing protein formulation to the polymer solution to form a polymer/protein mixture. The biologically active acid-stable or free sulfhydryl-containing protein formulation can be soluble or insoluble in the polymer solution.

Optional homogenization of the polymer/protein mixture.

Atomization of the polymer/protein mixture by sonication, and freezing of the droplets by contact with liquid nitrogen.

Extraction of the polymer solvent from the polymer/protein droplets into an extraction solvent (e.g., −80° C. ethanol), thereby forming particles comprising a polymer/stabilized protein matrix.

Isolation of the particles from the extraction solvent by filtration.

Removal of remaining solvent by evaporation.

Sizing of particles by passage through an appropriately sized mesh so as to produce an injectable product.

EXAMPLE 1

Preparation of Stabilized β-IFN Lyophilizate

Excipients were identified that stabilized β-IFN through the spray freeze drying process steps necessary to prepare the stabilized β-IFN formulation for encapsulation. Table 1 lists formulations of β-IFN initially investigated in assessing agents as potential stabilizers of β-IFN. Briefly, an aqueous solution containing the protein and the desired excipients, is sprayed into liquid nitrogen by pumping it through an ultrasonic nozzel. The resulting slurry of ice crystals and liquid nitrogen is kept at about −20 to −40° C. until the liquid nitrogen evaporates. The frozen solution is freeze-dried in a programmable lyophilizer (FTS Systems) over the course of three days.

The formulations from Table 1 which are listed in Table 2 are those which resulted in a β-IFN formulation which was as stable as bulk drug substance (BDS) after the initial spray freeze drying step of the process. Stability was assessed using SDS-PAGE and SEC methods as described above. The β-IFN formulations which gave values of % monomer greater than lyophilized bulk drug (Control) were determined as being stabilized β-IFN formulations.

TABLE 1

Composition of β-IFN Formulations

| β-IFN Formulation No. | Composition (% (w/w) of the solid formulation) |
|---|---|
| 1 | 90% sodium acetate, 10% β-IFN |
| 2 | 83% trehalose, 10% β-IFN, 7% acetate buffer salts pH4 |
| 3 | 80% HSA, 10% β-IFN, 2% NaCl (from HSA solution) 8% acetate buffer salts pH4 |
| 4 | 82% sucrose, 10% β-IFN, 8% acetate buffer salts pH4 |
| 5 | 77% trehalose, 10% β-IFN, 4% zinc acetate 9% acetate buffer salts pH5 |
| 6 | 77% trehalose, 10% β-IFN, 4% zinc acetate 9% acetate buffer salts pH4 |
| 7 | 73% mannitol, 10% β-IFN, 10% glycine, 7% acetate buffer salts pH4 |

TABLE 1-continued

Composition of β-IFN Formulations

| β-IFN Formulation No. | Composition (% (w/w) of the solid formulation) |
|---|---|
| 8 | 73% mannitol, 10% β-IFN, 10% PEG 8000, 7% acetate buffer salts pH4 |
| 9 | 80% mannitol, 10% β-IFN, 10% buffer salts (acetate + bicarbonate) pH7.7 |
| 10 | 63% mannitol, 10% β-IFN, 10% cysteine, 17% acetate buffer salts pH4 |
| 11 | 80% ammonium sulfate, 10% β-IFN, 10% acetate buffer salts pH4 |
| 12 | 80% ammonium sulfate, 10% β-IFN, 1% Tween 80, 9% acetate buffer salts pH4 |
| 13 | 80% ammonium sulfate, 10% β-IFN, 10% phosphate buffer salts pH5 |
| 14 | 70% mannitol, 10% β-IFN, 9% beta-cyclodextrin 11% buffer salts (acetate + bicarbonate) pH7 |

Formulation pH is of solution prior to lyophilization. If no pH listed, the pH was about 4.

TABLE 2

| | Integrity | |
|---|---|---|
| β-IFN Formulation No. | % Monomer (SEC) | % Monomer Area (SDS-PAGE) |
| BDS (0.35 mg/mL solution) | 98 | 85–92 |
| 1 | 92 | 74 |
| 2 | 96–98 | 85–90 |
| 3 | nb | 83–87 |
| 4 | 98 | 81 |
| 5 | 97 | 86 |
| 6 | 97 | 83 | nb: SEC could not be used due to interference with HSA. BDS = Bulk Drug Substance

EXAMPLE 2

Encapsulation of Lyophisizate Formulations

Stabilized β-IFN formulations 2, 3 and 6 were encapsulated into biocompatible polymers A, B, and C described above, employing the process outlined above with a target load of β-IFN of about 1%. Table 3 lists the various characteristics of the prepared microparticle formulations. The data suggests that the stabilized β-IFN lyophilizates are not deleteriously effected by the encapsulation process, and that the encapsulation efficiency of the stabilized β-IFN is high.

TABLE 3

Microparticle Characterization

| Microparticle Formulation No. | β-IFN Formulation No. | Polymer Type Used | % Protein | Microsphere Particle Size (Volume Median Diameter μm) | % β-IFN Monomer by SEC | % Native β-IFN by rHPLC |
|---|---|---|---|---|---|---|
| I | 3 | B | 1.0* | 56 | NQ | 99 |
| II | 3 | A | 1.0* | 63 | NQ | 99 |
| III | 3 | C | 1.0* | 62 | NQ | 100 |

TABLE 3-continued

Microparticle Characterization

| Microparticle Formulation No. | β-IFN Formulation No. | Polymer Type Used | % Protein | Microsphere Particle Size (Volume Median Diameter μm) | % β-IFN Monomer by SEC | % Native β-IFN by rHPLC |
|---|---|---|---|---|---|---|
| IV | 2 | B | 1.0 | 63 | 98 | 98 |
| V | 2 | A | 0.9 | 57 | 97 | 98 |
| VI | 2 | C | 1.0 | 57 | 96 | 97 |
| VII | 2 | A (w/zinc citrate) | 0.9 | 61 | 97 | 97 |
| VIII | 6 | A | 0.9 | 54 | 97 | 98 |

*Estimated from % nitrogen minus nitrogen due to HSA
NQ = Not Quantifiable due to HSA interference EXAMPLE 3
Preparation of β-IFN Formulations Having Post Hydration Stability A water-jacketed incubator (purchased from Forma Scientific) having a 100% humidity level and a temperature of 37° C. was used to simulate conditions experienced by microparticle formulations following administration in vivo. Use of the humidity chamber allowed assessment of formulations without the need for encapsulating the stabilized β-IFN in the polymer.

The β-IFN lyophilizate compositions tested are set forth in Table 4. Following incubation for 1 day monomer content was evaluated using SEC as described above. The humidity exposed stabilized β-IFN formulations were dissolved in a solution of 80% acetic acid/0.5% TWEEN® 80. The change in % monomer was determined by SEC and is listed in Table 4.

TABLE 4

| β-IFN Formulation No. | Composition (% W/W) | % Monomer (After 1 Day) Incubation in 100% Humidity |
|---|---|---|
| 15 | 10% β-IFN<br>80% Trehalose<br>10% Acetate | 56 |
| 16-1<br>16-2<br>16-3 | 10% β-IFN<br>12% Citrate<br>78% Trehalose | 42<br>55<br>80 |
| 17 | 10% β-IFN<br>12% Citrate<br>5% PLURONIC ® F68<br>73% Trehalose | 64 |
| 18 | 2.5% Tween ® 80<br>12% Citrate<br>10% β-IFN<br>75.5% Trehalose | 45 |
| 19 | 10% β-IFN<br>1% Tween ® 80<br>12% Citrate<br>77% Trehalose | 42 |
| 20 | 10% β-IFN<br>50% Citrate<br>40% Trehalose | 36 |
| 21 | 10% β-IFN<br>12% Citrate<br>5% PEG 8000<br>73% Trehalose | 63 ± 4 (COV: 6.3%) |
| 22 | 10% β-IFN<br>12% Citrate<br>0.5% PEG 8000<br>77.5% Trehalose | 48 ± 2.3 (COV: 4.8%) |
| 23 | 10% β-IFN<br>12% Citrate<br>5% PVP<br>73% Trehalose | 54 ± 4 (COV: 7.4%) |
| 24 | 10% β-IFN<br>12% Citrate<br>0.5% PVP<br>77.5% Trehalose | 59 ± 1.4 (COV: 2.3%) |
| 25-1<br>25-2 | 10% β-IFN<br>12% Glutamate<br>78% Trehalose | 88.0 ± 0.3 (COV: 0.3%)<br>84 |
| 26 | 10% β-IFN<br>12% Ascorbic Acid<br>78% Trehalose<br>12% Citrate | 79.0 ± 0.9 (COV: 1.1%) |

COV = Coefficient of Variation

The results presented in Table 4 show that the stabilized β-IFN Formulation 15 (Same components as Formulation 2 of Table 1), which was earlier determined to be stable to processing steps, did not sufficiently stabilize the β-IFN under conditions of hydration and likely release in vivo. Formulations 17, 21, 25 and 26 of Table 4, which all contain an acidic excipient were determined to be more stable than Formulation 15, and were therefore chosen for further investigation. Formulation 25 exhibited the greatest % increase in monomer over Formulation 15 (57% greater monomer content at Day 1). Formulation 16 exhibited low % monomer at Day 1 for two of the three batches tested. The data indicate that an acidic excipient is needed in the stabilized β-IFN formulation in order to minimize aggregation of β-IFN upon hydration.

EXAMPLE 4

Further Formulation Development

Additional formulations as well as ones described previously which contain various combinations of an acidic excipient and a disaccharide were prepared and tested in vitro for post hydration stability beyond one day of exposure to humidity. The stabilized β-IFN formulations were exposed to 100% humidity as detailed above. The presented in Table 5.

TABLE 5

| β-IFN Formulation No. | Composition | % Monomer of β-IFN Formulation (Humidification) Day 0 | Day 1 | Day 7 |
|---|---|---|---|---|
| 25 | 10% β-IFN/12% Glutamate/78% Trehalose | 98 | 84 | 79 |
| 27 | 10% β-IFN/30% Glutamate/60% Trehalose | 98 | 80 | 70 |
| 28 | 10% β-IFN/12% Aspartate/78% Trehalose | 98 | 81 | 70 |
| 29 | 10% β-IFN/25% Ascorbate/65% Trehalose | 98 | 93 | 65 |
| 30 | 10% β-IFN/12% Glutamate/13% Ascorbate/65% Trehalose | 97 | 76 | 35 |

Stabilized β-IFN formulations were prepared using water soluble polymers. The stability of the formulations was evaluated over 7 days at 37° C. and 100% humidity as earlier described. The results are presented in Table 6.

TABLE 6

| β-IFN Formulation No. | Composition | Humidification Results % Monomer Day 1 | Day 7 |
|---|---|---|---|
| 31 | 10% β-IFN/13% Glutamate/20% F68/ 57% Trehalose | 71 | 56 |
| 32 | 10% β-IFN/13% Glutamate/10% F127/67% Trehalose | 86 | 79 |
| 33 | 10% β-IFN/13% Glutamate/20% F127/57% Trehalose | 88 85 89 | 82 78 80 |
| 34 | 10% β-IFN/13% Glutamate/10% PEG 8000/67% Trehalose | 85 88 | 80 84 |
| 35 | 10% β-IFN/13% Glutamate/20% PEG 8000/57% Trehalose | 85 | 81 |
| 36 | 10% β-IFN/13% Glutamate/20% Methyl Cellulose/57% Trehalose | 91 98 98 | 84 83 93 |
| 37 | 10% β-IFN/ 12% Glutamate/5% F68/73% Trehalose | 82 | 65 |
| 38 | 10% β-IFN/ 12% Glutamate/10% F68/68% Trehalose | 86 | 73 |
| 39 | 10% β-IFN/12% Aspartate/10% F68/68% Trehalose | 82 82 | 72 68 |

TABLE 7

Incubation at 37° C., 100% Humidity

| β-IFN Formulation No. | Composition | pH of Dissolution Buffer | Incubation Time (Days) | % β-IFN Dissolved |
|---|---|---|---|---|
| 33 | 10% β-IFN/13% Glutamate/ 20% F127/57% Trehalose | 3.8<br><br>7 | 0<br>1<br>1 | 101<br>91<br>48 |
| 33 | 10% β-IFN/ 13% Glutamate/ 20% F127/57% Trehalose | 3.8<br><br>7 | 0<br>1<br>1 | 92<br>82<br>49 |
| 40 | 10% β-IFN/ 13% Aspartate/ 20% F127/57% Trehalose | 3.8<br><br>7 | 0<br>1<br>1 | 95<br>38<br>28 |
| 34 | 10% β-IFN/ 13% Glutamate/ 10% PEG 8000/ 57% Trehalose | 3.8<br><br>7 | 0<br>1<br>1 | 101<br>83<br>52 |
| 35 | 10% β-IFN/ 13% Glutamate/ 20% PEG 8000/ 57% Trehalose | 3.8<br><br>7 | 0<br>1<br>1 | 93<br>83<br>42 |
| 36 | 10% β-IFN/ 13% Glutamate/ 20% Methyl Cellulose/57% Trehalose | 3.8<br><br>7 | 0<br>1<br>1 | 100<br>94<br>66 |

The results presented in Table 6 indicate that stability of the β-IFN formulation increased by the presence of a water soluble polymer.

EXAMPLE 5

Figure 1:
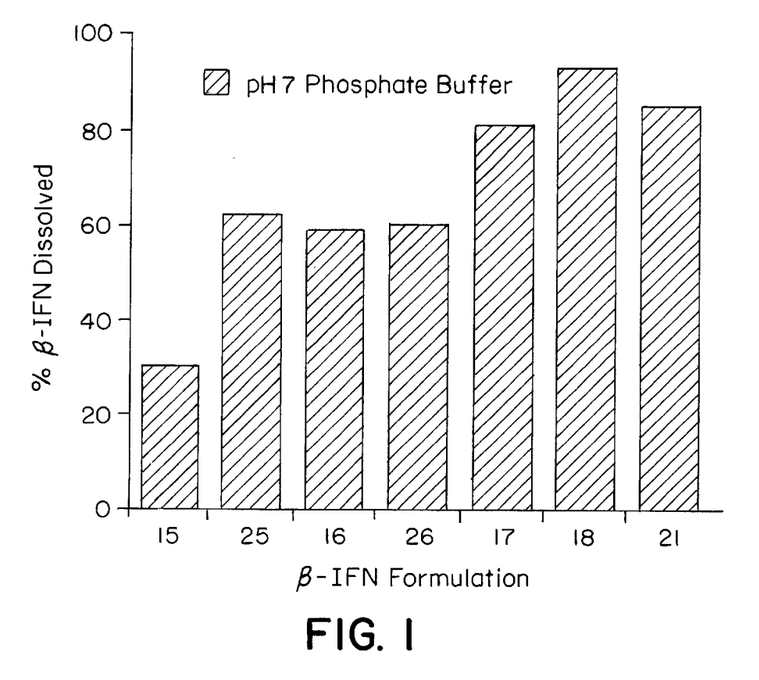
FIG. 1 is a graph of the % of β-IFN dissolved following incubation at 37° C. for one hour in pH 7 phosphate buffer for particular β-IFN formulations described in Table 4.

Evaluation of Lyophilizate Dissolution Before and After Hydration formulations 15, 16, 17, 18, 21, 25 and 26 of Table 4 were evaluated for phosphate buffer at pH 7. Each of the stabilized β-IFN formulations evaluated were added to phosphate buffer at pH 7 at a concentration of approximately 2 mg/mL of β-IFN, and then incubated at 37° C. for one hour. The samples were then centrifuged to remove precipitates and the supernatant was diluted in 250 mM acetate buffer for analysis by the Bio-Rad Protein Assay available from Bio-Rad Laboratories. The dissolution results are presented graphically in FIG. 1. FIG. 1 shows that a significant increase in dissolution is achieved with the presence of an acidic excipient alone or in combination with a water soluble polymer.

Additional formulations were prepared and evaluated for dissolution after one day of exposure to humidity. The dissolution of the humidified formulations was determined at both pH 3.8 (acetate buffer) and pH 7 (phosphate buffer) at a target concentration of at least 200 μg/mL of β-IFN. As controls, dissolution of non-humidified formulations in acetate buffer (pH 3.8) was also determined. The actual concentration of β-IFN in the solutions was measured using SEC.

EXAMPLE 6

Determination of Adsorption of β-IFN to a Biodegradable Polymer

Figure 2:
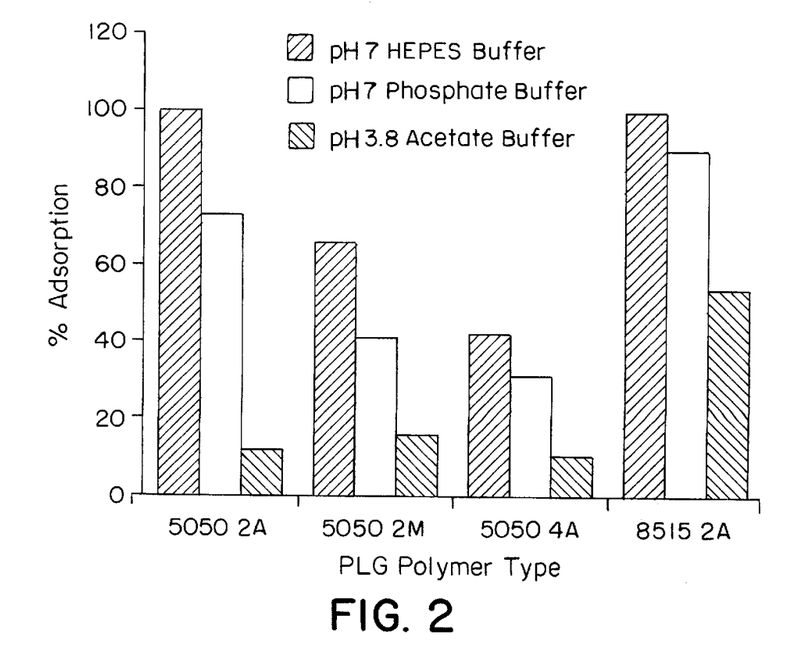
FIG. 2 is a graph of the % of β-IFN adsorbed on various biocompatible polymer microparticles following incubation of the microparticles with stabilized β-IFN Formulation 24 of Table 4.
Figure 3:
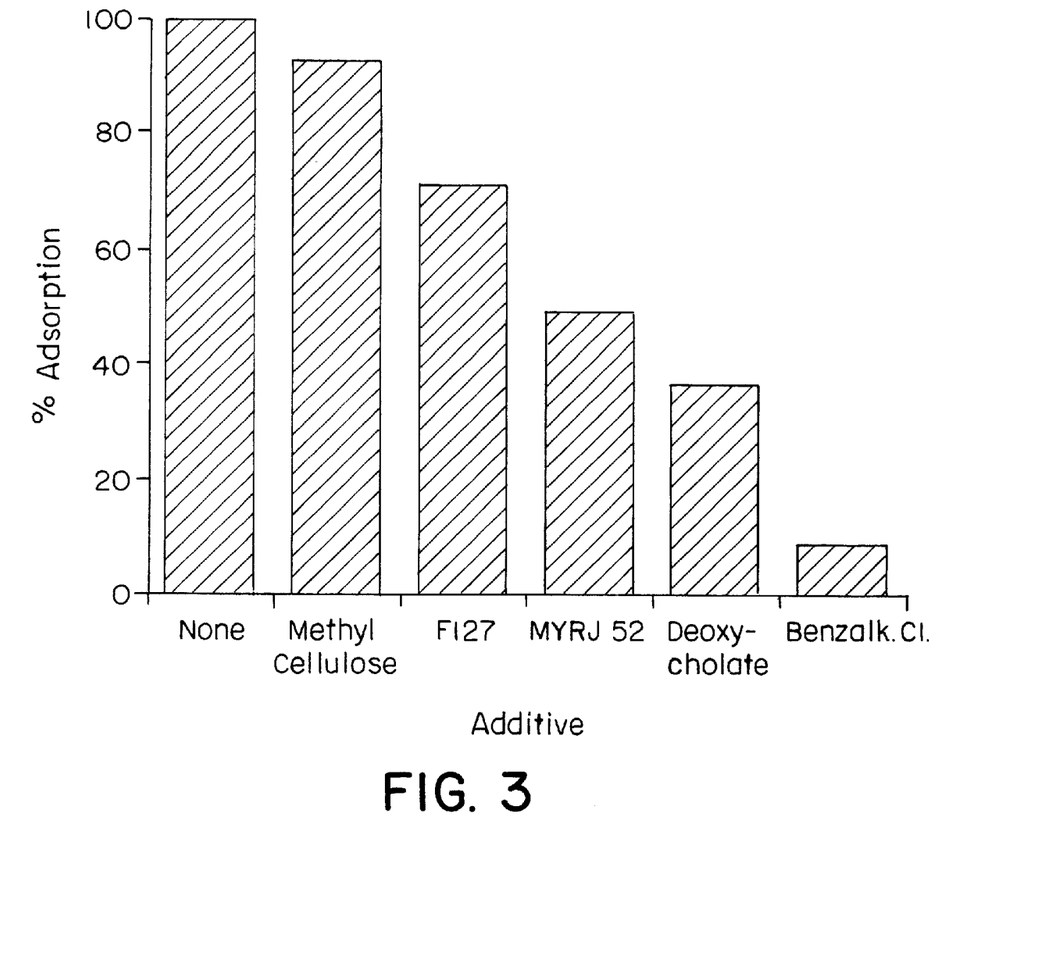
FIG. 3 is a graph of the % of β-IFN adsorbed on polymer microparticles following incubation with a stabilized β-IFN and various surfactants.
Figure 4:
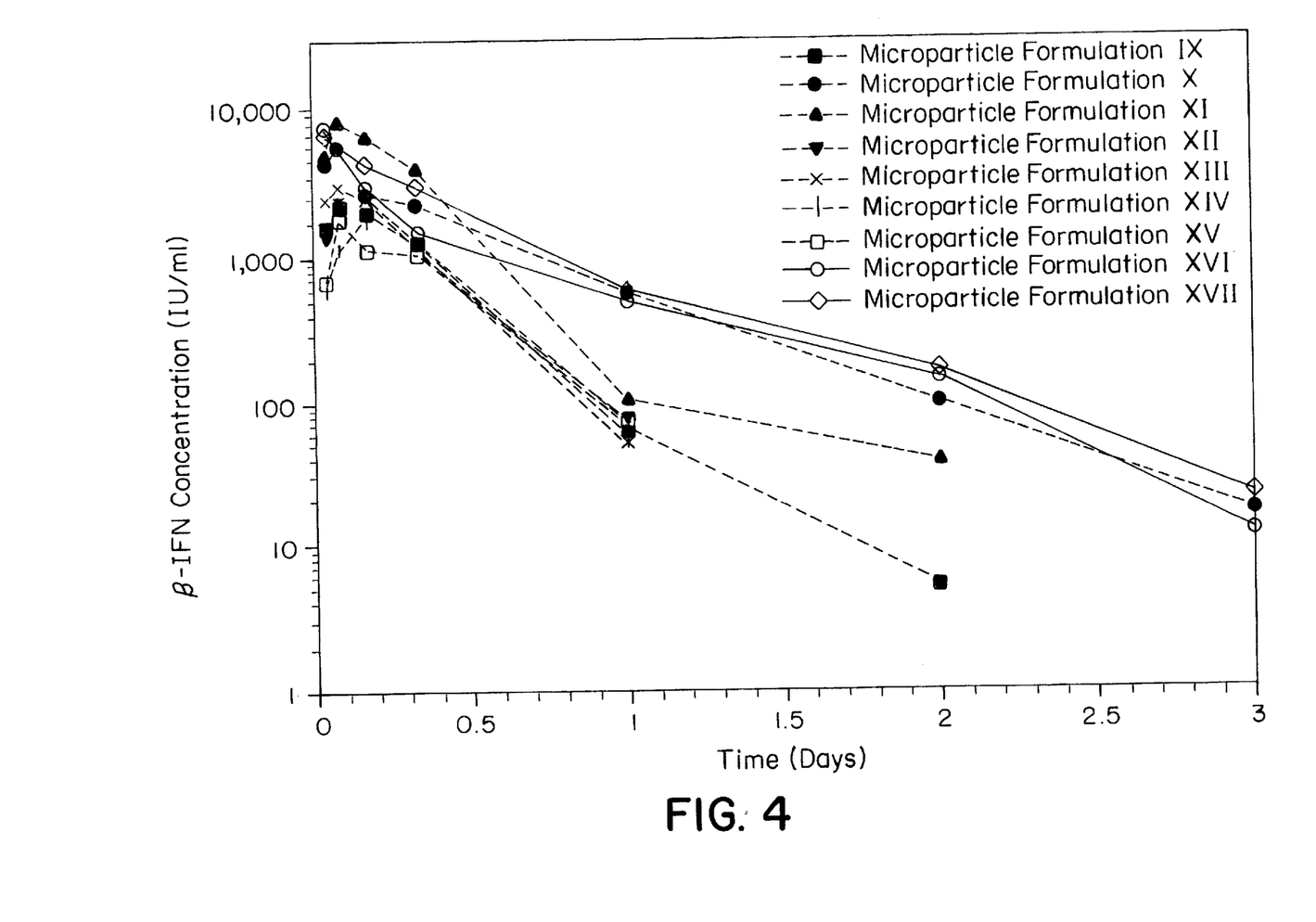
FIG. 4 is a graph of β-IFN serum concentration in rats receiving formulations containing excipients in the polymer phase to minimize adsorption of β-IFN to the biocompatible polymer matrix.

Experiments were performed to determine whether stabilized β-IFN formulations would be adsorbed onto the biocompatible polymer of the sustained release composition. The stabilized β-IFN Formulation 15 was added to three buffers (pH=3.8 acetate, pH=7 phosphate, and pH=7 HEPES) in an amount sufficient to achieve a concentration of 2 mg stabilized formulation/mL (~0.2 mg β-IFN /mL). Four batches of polymer microparticles were prepared as described above using polymers A–D also described above. 10 mg of each microparticle batch was added to 0.5 mL of each buffer. The β-IFN concentration in the supernatant was determined using SEC after two hours at 37° C. followed by centrifugation. The % adsorption was determined by comparing the concentrations of the samples exposed to polymer to control samples without polymer using the following equation:

% Adsorption=[1−Sample concentration/Control concentration (no polymer)]×100

The results are presented graphically in FIG. 2. The results show that β-IFN adsorbs to the polymers evaluated. In addition, the extent of adsorption depends on other factors such as buffer type, pH and polymer type.

EXAMPLE 7

Effect of Additives on Adsorption of β-IFN to Polymer

Stabilized β-IFN Formulation 36 was added to pH=7 phosphate buffer containing the following additives at a concentration of 4 mg/mL: methyl cellulose, F127, MYRJ 52, deoxycholate, and benzalkonium chloride. MYRJ 52 is commonly referred to as Polyoxy 40 Stearate of Polyoxyethylene (40) Monostearate and is a member of the general class of polyoxyethylene fatty acid esters. The final concentration of β-IFN was 0.2 mg/nL. 0.5 mL of each mixture was added to about 10 mg of microparticles prepared using Polymer D. The slurries were incubated at 37° C. for two hours. Each supernatant was isolated by centrifugation, diluted with an equal volume of 250 mM acetate buffer, and the concentration of β-IFN determined by SEC. Percent adsorption was calculated according to the formula provided in Example 6. The results are presented graphically in FIG. 3.

EXAMPLE 8

Effect of Formulation Additives of Release In Vivo

Microparticles were produced as described above using Stabilized β-IFN Formulation 39 (10% β-IFN/12% Aspartate/10% F68/68% Trehalose) and 33, and Polymer A. A description of each microparticle formulation is shown in Table 8.

The in vivo release profile for each microparticle formulation is shown in FIG. 4. Briefly, cyclosporin immunosuppressed male Sprague-Dawley rats weighing approximately 450 g were injected subcutaneously in the mid scapular region with 45 mgs of microparticle formulations IX-XVII listed in Table 8. Blood samples were taken at 1, 2, 4, 8, 24, 48 and 72 hours. β-IFN concentration in the samples was determined using an ELISA available from Toray-Fuji Bionics, Inc. (TFB, Inc.). The results are shown graphically in FIG. 4.

The release profiles in FIG. 4 show that the presence of a poloxamer significantly increased the total amount of β-IFN released as compared to the same formulation without poloxamer. The presence of an acidic excipient also demonstrated an increase in the total amount of β-IFN released during the time evaluated, but the increase was much less than that seen with the poloxamer. In addition, the combination of poloxamer and acidic excipient (Formulation XVII) showed an increase over surfactant alone. All profiles in FIG. 4 were normalized to a dose of 0.45 mg β-IFN per rat.

TABLE 8

| Microparticle Formulation No. | β-IFN Formulation Encapsulated | Polymer Phase Additive |
|---|---|---|
| IX | 39 | None |
| X | 39 | 20% F127 |
| XI | 39 | 20% F68 |
| XII | 39 | 20% PEG 8000 |
| XIII | 39 | 15% Aspartic Acid |
| XIV | 39 | 13.5% Aspartic Acid/1.5% Zinc Citrate |
| XV | 33 | None |
| XVI | 33 | 20% F127 |
| XVII | 33 | 20% F127 15% Sodium Citrate |

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A solid composition for the sustained release of biologically active acid-stable or free sulfhydryl-containing protein comprising:

a) a biocompatible polymer;

b) particles of a stabilized biologically active acid-stable or free sulfhydryl-containing protein formulation comprising at least one biologically active acid-stable or free sulfhydryl-containing protein, at least one disaccharide and at least one acidic excipient; and c) surfactant wherein said biologically active protein formulation and said surfactant are dispersed within the biocompatible polymer.

2. The sustained release composition of claim 1 wherein the biologically active acid-stable or free sulfhydryl-containing protein is β-IFN.

3. The sustained release composition of claim 2 wherein the β-IFN is present in the stabilized formulation from about 0.5% (w/w) to about 50% (w/w) of the dry weight of the formulation.

4. The sustained release composition of claim 3 wherein the β-IFN is present in a range from about 0.5% (w/w) to about 30% (w/w) of the dry weight of the formulation.

5. The sustained release composition of claim 1 wherein the acidic excipient is an organic acid.

6. The sustained release composition of claim 5 wherein the organic acid is selected form the group consisting of: citric acid, ascorbic acid, acetic acid, ethylenediamninetetraacetic acid, saturated fatty acids, dicarboxylic acids, bile acids, amino acids and combinations thereof.

7. The sustained release composition of claim 6 wherein the organic acid is an acidic amino acid.

8. The sustained release composition of claim 7 wherein the acidic amino acid is glutamic acid, aspartic acid or a combination thereof.

9. The sustained release composition of claim 1 wherein the disaccharide is selected from the group consisting of: sucrose, trehalose and combinations thereof.

10. The sustained release composition of claim 1 wherein the surfactant is selected from the group consisting of: poloxamers, polysorbates, polyethyleneglycols, polyoxyethylene fatty acid esters, bile salts, benzalkonium chloride, polyoxyethylene (40) monostearate and combinations thereof.

11. The sustained release composition of claim 1 further comprising an acidic excipient which is separately dispersed within the biocompatible polymer.

12. The sustained release composition of claim 10 wherein the poloxamer is selected from the group consisting of: poloxamer 407, poloxamer 188, and combinations thereof.

13. The sustained release composition of claim 10 wherein the polysorbate is selected from the group consisting of: polysorbate 80, polysorbate 20 and combinations thereof.

14. The sustained release composition of claim 1 wherein the biologically active protein is present from about 0.01% (w/w) to about 30% (w/w) of the total weight of the sustained release composition.

15. The sustained release composition of claim 14 wherein the protein is present from about 0.5% (w/w) to about 5% (w/w) of the total weight of the sustained release composition.

16. The sustained release composition of claim 1 wherein the stabilized biologically active acid-stable or free sulfhydryl-containing protein formulation further comprises a water soluble polymer.

17. The sustained release composition of claim 16 wherein the water soluble polymer is a polysaccharide.

18. The sustained release composition of claim 17 wherein the polysaccharide is selected from the group consisting of: methyl cellulose, ethylcellulose, ficoll, and combinations thereof.

19. The sustained release composition of claim 16 wherein the water soluble polymer is a polymer surfactant.

20. The sustained release composition of claim 19 wherein the polymer surfactant is nonionic.

21. The sustained release composition of claim 20 wherein the nonionic surfactant is selected from the group consisting of: poloxamers, polysorbates, polyethyleneglycol, polyoxyethlene fatty acid esters and combinations thereof.

22. The sustained release composition of claim 21 wherein the poloxamer is selected from the group consisting of: poloxamer 188, poloxamer 407 and combinations thereof.

23. The sustained release composition of claim 21 wherein the polysorbate is selected from the group consisting of: polysorbate 80, polysorbate 20 and combinations thereof.

24. The sustained release composition of claim 1 wherein the biocompatible polymer is selected from the group consisting of: poly(lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends thereof and copolymers thereof.

25. The sustained release composition of claim 24 wherein said polymer comprises poly(lactide-co-glycolide).

26. The sustained release composition of claim 1 further comprising a multivalent metal cation component dispersed within the biocompatible polymer.

27. A method for delivering a biologically active acid-stable or free sulfhydryl-containing protein to a subject for a sustained period comprising administering to the subject a dose of the sustained release composition of claim 1.

28. A method for forming a composition for the sustained release of a biologically active acid-stable or free sulfhydryl-containing protein, comprising the steps of:
   a) dissolving a biocompatible polymer in a polymer solvent to form a polymer solution;
   b) adding at least one surfactant and a stabilized biologically active acid-stable or free sulfhydryl-containing protein formulation comprising: at least one biologically active acid-stable or free sulfhydryl-containing protein; at least one disaccharide; and at least one acidic excipient, to the polymer solution; and
   c) solidifying the biocompatible polymer to form a polymer matrix containing the stabilized biologically active protein formulation and the surfactant dispersed therein.

29. The method of claim 28 wherein the biologically active acid-stable or free sulfhydryl-containing protein is β-IFN.

30. The method of claim 29 wherein the β-IFN is present in the stabilized formulation from about 0.5% (w/w) to about 50% (w/w) of the dry weight of the formulation.

31. The method of claim 30 wherein the β-IFN is present in a range from about 0.5% (w/w) to 30% (w/w) of the dry weight of the formulation.

32. The method of claim 28 wherein the acidic excipient is an organic acid.

33. The method of claim 32 wherein the organic acid is selected form the group consisting of: citric acid, ascorbic acid, acetic acid, ethylenediaminetetraacetic acid, saturated fatty acids, dicarboxylic acids, bile acids, and combinations thereof.

34. The method of claim 33 wherein the organic acid is an acidic amino acid.

35. The method of claim 34 wherein the acidic amino acid is glutamic acid, aspartic acid or a combination thereof.

36. The method of claim 28 wherein the disaccharide is selected from the group consisting of: sucrose, trehalose and combinations thereof.

37. The method of claim 28 wherein the surfactant is selected from the group consisting of: poloxamers, polysorbates, polyethylene glycol, polyoxyethlene fatty acid esters, bile salts, benzalkonium chloride and combinations thereof.

38. The method of claim 37 wherein the poloxamer is selected from the group consisting of: poloxamer 407, poloxamer 188 and combinations thereof.

39. The method of claim 37 wherein the polysorbate is selected from the group consisting of: polysorbate 80, polysorbate 20 and combinations thereof.

40. The method of claim 28 wherein the biologically active acid-stable or free sulfhydryl-containing protein is present from about 0.01% (w/w) to about 30% (w/w) of the total weight of the sustained release composition.

41. The method of claim 40 wherein the protein is present from about 0.5% (w/w) to about 5% (w/w) of the total weight of the composition.

42. The method of claim 30 wherein the stabilized biologically active β-IFN formulation further comprises a water soluble polymer.

43. The method of claim 42 wherein the water soluble polymer is a polysaccharide.

44. The method of claim 43 wherein the polysaccharide is selected from the group consisting of: methyl cellulose, ethyl cellulose, ficoll and combinations thereof.

45. The method of claim 42 wherein the water soluble polymer is a polymer surfactant.

46. The method of claim 45 wherein the polymer surfactant is nonionic.

47. The method of claim 46 wherein the nonionic surfactant is selected from the group consisting of: poloxamers, polysorbates, polyethyleneglycol, polyoxyethylene fatty acid esters, and combinations thereof.

48. The method of claim 47 wherein the poloxamer is selected from the group consisting of: poloxamer 407, poloxamer 188, and combinations thereof.

49. The method of claim 47 wherein the polysorbate is selected from the group consisting of: polysorbate 80, polysorbate 20, and combinations thereof.

50. The method of claim 28 wherein the biocompatible polymer is selected from the group consisting of poly(lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends thereof and copolymers thereof.

51. The method of claim 50 wherein said polymer comprises poly(lactide-co-glycolide).

52. The method of claim 28 further comprising the step of adding a multivalent metal cation component to the polymer solution.

53. A solid composition for the sustained release of biologically active acid-stable or free sulfhydryl-containing protein comprising:

a) a biocompatible polymer;
b) particles of a stabilized biologically active acid-stable or free sulfhydryl-containing protein formulation comprising at least one biologically active acid-stable or free sulfhydryl-containing protein selected from interleukin-2, basic fibroblast growth factor, granulocyte colony stimulating factor, IFN-β, megakaryocyte growth and differentiation factor, tissue plasminogen activator, insulin-like growth factor-1 and interleukin-1β, at least one disaccharide and at least one acidic excipient; and
c) surfactant wherein said biologically active protein formulation and said surfactant are dispersed within the biocompatible polymer.

* * * * *